(12) United States Patent
Migukin et al.

(10) Patent No.: US 11,080,847 B2
(45) Date of Patent: Aug. 3, 2021

(54) MAGNETIC RESONANCE IMAGING DEVICE AND METHOD FOR GENERATING MAGNETIC RESONANCE IMAGE

(71) Applicant: SAMSUNG ELECTRONICS CO., LTD., Suwon-si (KR)

(72) Inventors: Artem Sergeevich Migukin, St. Petersburg (RU); Dmitry Alexandrovich Korobchenko, Moscow (RU); Mikhail Yurievich Sirotenko, Moscow (RU); Kirill Arthurovich Gavrilyuk, Moscow (RU); Praveen Gulaka, Suwon-si (KR); Sang-cheon Choi, Seoul (KR); Michail Nikolaevich Rychagov, Moscow (RU); Yang Lim Choi, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1259 days.

(21) Appl. No.: 15/307,936

(22) PCT Filed: Apr. 30, 2015

(86) PCT No.: PCT/KR2015/004446
§ 371 (c)(1),
(2) Date: Oct. 31, 2016

(87) PCT Pub. No.: WO2015/167307
PCT Pub. Date: Nov. 5, 2015

(65) Prior Publication Data
US 2017/0053402 A1    Feb. 23, 2017

(30) Foreign Application Priority Data

Apr. 30, 2014  (RU) ........................... RU2014117696
Dec. 31, 2014  (KR) ........................ 10-2014-0195373

(51) Int. Cl.
*G06T 7/00*    (2017.01)
*A61B 5/055*   (2006.01)
(Continued)

(52) U.S. Cl.
CPC ............ *G06T 7/0012* (2013.01); *A61B 5/055* (2013.01); *A61B 5/7257* (2013.01);
(Continued)

(58) Field of Classification Search
None
See application file for complete search history.

(56) References Cited

U.S. PATENT DOCUMENTS 8,310,233 B2    11/2012  Trzasko et al.
2005/0228261 A1 10/2005  Huber et al.
(Continued)

FOREIGN PATENT DOCUMENTS

| CN | 103142228 A | 6/2013 |
|---|---|---|
| KR | 101283532 B1 | 7/2013 |
| RU | 2479038 C2 | 4/2013 |

OTHER PUBLICATIONS

Ravishankar et al. ("Multiscale Dictionary Learning for MRI", Proc. Intl. Soc. Mag. Res. Med. 19, 2011 (Year: 2011).*
(Continued)

*Primary Examiner* — Pascal M Bui Pho
*Assistant Examiner* — Marjan Saboktakin
(74) *Attorney, Agent, or Firm* — Sughrue Mion, PLLC

(57) ABSTRACT

Provided is a magnetic resonance imaging (MRI) apparatus including an acquisition unit configured to acquire an undersampled spectrum in a k-space and a reconstruction unit configured to generate a target image based on the undersampled spectrum, wherein the reconstruction unit includes: a first sub-reconstruction unit configured to perform initial reconstruction on data corresponding to unsampled posi-
(Continued)

tions in the k-space by using a Split Bregman algorithm or approximate sparse coding; a second sub-reconstruction unit configured to decompose the initially reconstructed spectrum in the k-space into multiple frequency bands to thereby generate a plurality of individual spectra and perform dictionary learning reconstruction on images respectively corresponding to the decomposed multiple frequency bands by alternating sparse approximation and reconstructing of measured frequencies; and an image generator configured to generate a target image by merging together the reconstructed images respectively corresponding to the multiple frequency bands.

7 Claims, 8 Drawing Sheets

(51) Int. Cl.
    *A61B 5/00*     (2006.01)
    *G01R 33/561*     (2006.01)
    *G06T 11/00*     (2006.01)

(52) U.S. Cl.
    CPC ........ *G01R 33/5611* (2013.01); *G06T 11/003* (2013.01); *A61B 2576/00* (2013.01); *G06T 2207/10088* (2013.01); *G06T 2207/20081* (2013.01)

(56) References Cited

U.S. PATENT DOCUMENTS

| | | |
|---|---|---|
| 2006/0029279 A1 | 2/2006 | Donoho |
| 2007/0110290 A1 | 5/2007 | Chang et al. |
| 2011/0080166 A1 | 4/2011 | Edelman et al. |
| 2012/0177128 A1 | 7/2012 | Aharon et al. |
| 2012/0259590 A1 | 10/2012 | Ye et al. |
| 2013/0099786 A1 | 4/2013 | Huang et al. |
| 2013/0279786 A1 | 10/2013 | Lin et al. |

OTHER PUBLICATIONS

Communication dated Aug. 13, 2015, issued by the International Searching Authority in counterpart International Application No. PCT/KR2015/004446 (PCT/ISA/220, 210, 237).
Communication dated Jul. 22, 2015, issued by the Russian Patent Office in counterpart Russian Application No. 2014117696/08.
Bo Liu et al., "Regularized Sensitivity Encoding (SENSE) Reconstruction Using Bregman Iterations", Magnetic Resonance in Medicine 61, 2009, pp. 145-152.
Saiprasad Ravishankar and Yoram Bresler, "MR Image Reconstruction From Highly Undersampled k-Space Data by Dictionary Learning", IEEE Transactions on Medical Imaging, vol. 30, No. 5, May 2011, pp. 1028-1041.
Artem Migukin et al., "Phase retrieval in 4f optical system: background compensation and sparse regularization of object with binary amplitude", Applied Optics, Jan. 1, 2013, vol. 52, No. 1, pp. A269-A280.
Qiegen Liu et al., "Highly Undersampled Magnetic Resonance Image Reconstruction Using Two-Level Bregman Method With Dictionary Updating", IEEE Transactions on Medical Imaging, vol. 32, No. 7, Apr. 2, 2013, pp. 1290-1301, XP011516357. (12 pages total).
E. Gong et al., "MRI Reconstruction by Learning the Dictionary of Spatial frequency-Bands Correlation A novel algorithm integratable with PI and CS to further push acceleration", Proceedings of the International Society for Magnetic Resonance in Medicine, 22nd Annual Meeting and Exhibition, Milan, Italy, vol. 22, Apr. 25, 2014, p. 0744, XP040661824. (1 page total).
V. P. Gopi et al., "MR image reconstruction based on framelets and nonlocal total variation using split Bregman method", International Journal of Computer Assisted Radiology and Surgery, vol. 9, No. 3, Sep. 8, 2013, pp. 459-472, XP055459138. (14 pages total).
Communication dated May 7, 2018 by the European Patent Office in counterpart European Patent Application No. 15785798.8.

\* cited by examiner

MAGNETIC RESONANCE IMAGING DEVICE AND METHOD FOR GENERATING MAGNETIC RESONANCE IMAGE

This application is a National stage entry of International Application No. PCT/KR2015/004446, filed on Apr. 30, 2015, which claims priority from Russian Patent Application No. 2014117696, filed on Apr. 30, 2014 in the Russian Patent Office, and Korean Patent Application No. 10-2014-0195373, filed on Dec. 31, 2014 in the Korean Intellectual Property Office. The disclosures of each of the applications are herein incorporated by reference in their entirety.

TECHNICAL FIELD

The present invention relates to medical imaging, and more particularly, to a method and system for reconstructing a target image from undersampled data. The present invention may be applied to MRI scanners for accelerating image acquisition and be implemented as software or hardware components of medical equipment.

BACKGROUND ART

Magnetic resonance imaging (MRI) is a noninvasive and nonionizing imaging technique, which is widely utilized in diagnosis due to its excellent ability to visualize both an anatomical structure and a physiological function. However, MRI is a relatively slow imaging modality since pieces of used data, i.e., samples of the spatial Fourier transform of an object in the so-called k-space, are acquired sequentially over time.

Due to the long image acquisition time, a patient that is within a bore of an MRI apparatus may feel uncomfortable in a confined space, and acquisition of MR images is uneconomical. Thus, there is a need for a technique and MRI apparatus for obtaining images at a high speed.

DETAILED DESCRIPTION OF THE INVENTION

Technical Problem

Provided are magnetic resonance imaging (MRI) apparatuses and methods whereby a magnetic resonance (MR) image can be obtained in a shorter time.

Technical Solution

According to an aspect of an embodiment, an MRI apparatus includes: an acquisition unit configured to acquire an undersampled spectrum in a k-space; and a reconstruction unit configured to generate a target image based on the undersampled spectrum, wherein the reconstruction unit includes: a first sub-reconstruction unit configured to perform initial reconstruction on data corresponding to unsampled positions in the k-space by using a Split Bregman algorithm or approximate sparse coding; a second sub-reconstruction unit configured to decompose the initially reconstructed spectrum in the k-space into multiple frequency bands to thereby generate a plurality of individual spectra and perform dictionary learning reconstruction on images respectively corresponding to the decomposed multiple frequency bands by alternating sparse approximation and reconstructing of measured frequencies; and an image generator configured to generate a target image by merging together the reconstructed images respectively corresponding to the multiple frequency bands.

For example, the first sub-reconstruction unit may perform the approximate sparse coding by collecting a fully sampled k-space dataset, applying a sampling mask, preparing undersampled data according to an index of the sampling mask, training a model to predict sparse codes for the undersampled data by using fully sampled data for calculation of an error, and predicting approximated sparse codes from the undersampled data by using the trained model.

Sparse approximation may include extracting non-uniform sized overlapping patches from an input image corresponding to an input MR signal, performing sparse decomposition of the extracted non-uniform sized patches into sparse codes by using a dictionary, reconstructing the non-uniform sized patches by using the sparse codes and the dictionary, and reconstructing an image by using the reconstructed patches.

The dictionary may be learned in advance based on patches extracted from a set of fully-sampled training MR images.

The dictionary may be learned individually for each frequency band.

The sparse decomposition may be performed by minimizing a number of non-zero elements in a patch represented as a linear combination of dictionary elements.

An aspect ratio of the non-uniform sized patches may be determined according to the amount of anisotropy in a sampling scheme.

The patches may have a rectangular shape for Cartesian one-dimensional (1D) sampling and other anisotropic sampling schemes, and have a longest dimension in a direction along which most information is lost in an undersampled k-space.

The patches may have a square shape for an isotropic sampling scheme.

The dictionary learning reconstruction may be performed for each k-space corresponding to a different frequency band.

Each of k-spaces corresponding to the decomposed multiple frequency bands may be composed of frequencies acquired from an initially reconstructed k-space corresponding to a current band, while the other frequencies are filled with zeroes and marked as measured.

According to an aspect of another embodiment, a method, performed by an MRI apparatus, of generating an MR image from undersampled data includes: acquiring an undersampled spectrum in a k-space via a receiver coil; performing initial reconstruction by filling unsampled positions in the k-space with an initial guess; decomposing the initially reconstructed spectrum in the k-space into multiple frequency bands to thereby generate a plurality of individual spectra; performing dictionary learning reconstruction on images respectively corresponding to the decomposed multiple frequency bands; and generating a target image by merging together the images reconstructed by performing the dictionary learning reconstruction, a. wherein the performing of the initial reconstruction comprises optimizing a cost function including a simplified $l_0$ norm, b. wherein the decomposing of the initially reconstructed spectrum comprises decomposing the initially reconstructed spectrum in the k-space to obtain the plurality of individual spectra corresponding to the multiple frequency bands, c. wherein the performing of the dictionary learning reconstruction comprises alternating sparse approximation and reconstructing of measured frequencies, and d. wherein the generating of the target image comprises generating the target image as a sum of the reconstructed images corresponding to the multiple frequency bands.

$l_0$ norm regularization may be simplified via $l_1$ norm optimization.

The $l_1$ norm optimization may be implemented using a Split Bregman algorithm or approximate sparse coding According to an aspect of another embodiment, an MRI system includes: an acquisition unit configured to acquire an undersampled spectrum in a k-space via a receiver coil; and a reconstruction server configured to store the undersampled spectrum in the k-space transmitted by the acquisition unit, perform initial reconstruction by filling unsampled positions in the k-space with an initial guess, perform multiband decomposition of the initially reconstructed spectrum into multiple frequency bands to thereby generate a plurality of individual spectra, perform dictionary learning reconstruction on images respectively corresponding to the decomposed multiple frequency bands, and generate a target image by merging together the images reconstructed by performing the dictionary learning reconstruction, a. wherein the initial reconstruction is performed by optimizing a cost function including a simplified $l_0$ norm, b. wherein the multiband decomposition is applied to the initially reconstructed spectrum in the k-space to obtain the plurality of individual spectra corresponding to the multiple frequency bands, c. wherein the dictionary learning reconstruction is performed by alternating sparse approximation and reconstructing of measured frequencies, and d. wherein the target image is generated by summing the reconstructed images corresponding to the multiple frequency bands.

The MRI system may further include an operator console configured to receive a result of the merging from the reconstruction server and display the result of the merging on a display.

The operator console may receive an input from an operator in order to perform image reconstruction, generate an image reconstruction command, and transmit the image reconstruction command to the reconstruction server; and the reconstruction server may receive the image reconstruction command from the operator console and perform the image reconstruction.

Advantageous Effects of the Invention

According to the embodiments, an MR image may be reconstructed from undersampled Fourier spectral data at a high speed. Furthermore, sparse regularization may be performed by using precomputed dictionaries with image patches, which may accelerate the computational algorithms and improve reconstruction accuracy.

MODE OF THE INVENTION

Figure 1:
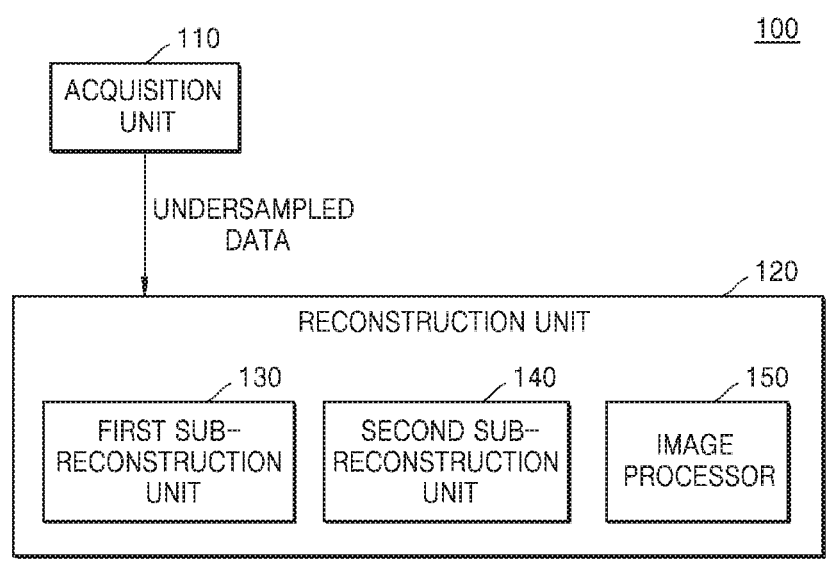
FIG. 1 is a block diagram of a magnetic resonance imaging (MRI) apparatus according to an embodiment.

The attached drawings for illustrating exemplary embodiments of the present disclosure are referred to in order to gain a sufficient understanding of the present disclosure, the merits thereof, and the objectives accomplished by the implementation of the present disclosure. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims.

Hereinafter, the terms used in the specification will be briefly described, and then the present disclosure will be described in detail.

The terms used in this specification are those general terms currently widely used in the art in consideration of functions regarding the present disclosure, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the embodiments of the present invention means a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to embodiments, examples of which are illustrated in the accompanying drawings. In the following description, well-known functions or constructions are not described in detail so as not to obscure the embodiments with unnecessary detail.

Throughout the specification, an "image" may mean multi-dimensional data formed of discrete image elements, e.g., pixels in a two-dimensional (2D) image and voxels in a three-dimensional (3D) image. For example, the image may be a medical image of an object captured by an X-ray apparatus, a computed tomography (CT) apparatus, a magnetic resonance imaging (MRI) apparatus, an ultrasound diagnosis apparatus, or another medical imaging apparatus.

Furthermore, in the present specification, an "object" may be a human, an animal, or a part of a human or animal. For example, the object may be an organ (e.g., the liver, the heart, the womb, the brain, a breast, or the abdomen), a blood vessel, or a combination thereof. The object may be a phantom. The phantom means a material having a density, an effective atomic number, and a volume that are approximately the same as those of an organism. For example, the phantom may be a spherical phantom having properties similar to the human body.

Furthermore, in the present specification, a "user" may be, but is not limited to, a medical expert, such as a medical doctor, a nurse, a medical laboratory technologist, or a technician who repairs a medical apparatus.

Furthermore, in the present specification, an "MR image" refers to an image of an object obtained by using the nuclear magnetic resonance principle.

Furthermore, in the present specification, a "pulse sequence" refers to continuity of signals repeatedly applied by an MRI apparatus. The pulse sequence may include a time parameter of a radio frequency (RF) pulse, for example, repetition time (TR) or echo time (TE).

Furthermore, in the present specification, a "pulse sequence schematic diagram" shows an order of events that occur in an MRI apparatus. For example, the pulse sequence schematic diagram may be a diagram showing an RF pulse, a gradient magnetic field, an MR signal, or the like according to time.

An MRI system is an apparatus for acquiring a sectional image of a part of an object by expressing, in a contrast comparison, a strength of a MR signal with respect to a radio frequency (RF) signal generated in a magnetic field having a specific strength. For example, if an RF signal that only resonates a specific atomic nucleus (for example, a hydrogen atomic nucleus) is emitted for an instant toward the object placed in a strong magnetic field and then such emission stops, an MR signal is emitted from the specific atomic nucleus, and thus the MRI system may receive the MR signal and acquire an MR image. The MR signal denotes an RF signal emitted from the object. An intensity of the MR signal may be determined according to a density of a predetermined atom (for example, hydrogen) of the object, a relaxation time $T_1$, a relaxation time $T_2$, and a flow of blood or the like.

In the present specification, a k-space may mean a matrix of spatial frequencies, which has a mathematical relationship to an image. In digitalized MRI signal data, each point in k-space represents a spatial frequency, and may further contain signal intensity information. Undersampled k-space data may be k-space data that do not satisfy the Nyquist criterion. Fully sampled k-space data may be k-space data satisfying the Nyquist criterion.

In general, an MRI apparatus may examine an internal structure of a human body by using energy induced due to resonance reactions after applying a signal having a specific frequency and energy to nuclei of atoms within a patient's body placed in a magnetic field.

A landmark compressed sensing (CS) technique, originated by Donoho [US patent application 2006/0029279], has demonstrated that sparse imaging allows reconstruction from fewer sampling data. That is, for accurate reconstruction of MR images, the k-space does not need to be fully sampled according to phase encoding steps in a pulse sequence. Thus, CS is a keynote for hardware-based acceleration of MRI.

Various algorithms may be used for CS reconstruction such as total variation [B. Liu et al., "Regularized Sensitivity Encoding (SENSE) reconstruction using Bregman iterations," Magnetic Resonance in Medicine 61, 145-152 (2009)] or $l_1$-regularized optimization, compressed sensing MRI via recomputing [S. Ravishankar and Y. Bresler, "Image reconstruction from highly undersampled k-space data by dictionary learning," IEEE Trans. on Med. Imag. 30, 1028-1041 (2011)] or a precomputed dictionary [A. Migukin et al., "Phase retrieval in 4f optical system: background compensation and sparse regularization of object with binary amplitude," Appl. Opt. 52, A269-A280 (2013)].

As described above, US patent application 2006/0029279 provides a groundbreaking framework in CS technology. It describes a technique for reconstructing signals/images with acceptable quality from fewer measurements than the number of unknowns. The main idea is to find a sparse representation of an object of interest with respect to an overcomplete basis. However, in the patent application, due to too general variational formulation of the optimization problem, it is necessary to specify a sparsifying transform.

US patent application 2007/0110290 describes a technique for reconstructing medical images from undersampled data measured in a k-space by an iterative minimization algorithm. In this patent application, the reconstruction is performed by using constrained optimization of a formulated and/or preformulated functional that comprises a norm of a sparse representation of a trial image derived from a dataset and/or a data fidelity term. The crucial point is that the minimization algorithm can comprise a conjugate gradient sub-algorithm and/or a Bregman iteration.

US patent application 2012/0177128 describes an adaptation procedure to design dictionaries for sparse representation of a signal/image by using the K-SVD algorithm. Based on one or more training signals, the described signal processing system provides a dictionary containing prototype signal-atoms-so that each training signal can be represented as a sparse linear combination of the dictionary's signal-atoms. The use of overcomplete and sparse representations is demonstrated via several efficient methods such as Matching Pursuit (MP), Orthogonal Matching Pursuit (OMP), Basis Pursuit (BP) and Focal Under-determined System Solver (FOCUSS) algorithms, which are motivated based on Maximum A Posteriori (MAP) estimation, the Maximum Likelihood (ML) method, the Independent Component Analysis (ICA) algorithm, and the Method of Optimal Direction (MOD).

US patent application 2012/0259590 describes a CS technique for reconstructing a signal/image from a plurality of measurement vectors when the signal corresponds to a plurality of jointly sparse vectors. This patent application provides a method of extracting information from a plurality of measurement vectors of jointly sparse signals and computing a subset with at least one element of a joint support based on the plurality of measurement vectors. Sparse recovery is formulated by computing a succinct representation or a sparse approximation to a given vector by a linear combination of a small number of vectors from a collection of vectors known as a dictionary.

The methods described in the cited references may have drawbacks in several aspects. Some of the techniques are oriented towards a very narrow specific task: specific prior information about the target object, its properties and/or type of used data are known. The vital part of each CS algorithm is its initialization: almost all authors publish results for a default zero-filling case. As a rule, dictionaries with uniform-sized patches are iteratively recalculated.

An MRI Apparatus for Reconstructing an MR Image from Undersampled Data

FIG. 1 is a block diagram of an MRI apparatus 100 according to an embodiment. Referring to FIG. 1, the MRI apparatus 100 may include an acquisition unit 110 and a reconstruction unit 120. The reconstruction unit 120 may include a first sub-reconstruction unit 130, a second sub-reconstruction unit 140, and an image processor 150.

The acquisition unit 110 may acquire an undersampled spectrum in k-space. The acquisition unit 110 may acquire undersampled data in k-space by using an MR signal received via a receiver coil. In detail, the acquisition unit 110 may acquire an MR signal from an object by applying an RF pulse having a specific frequency. The acquisition unit 110 may not acquire an MR signal for some spatial frequencies while acquiring an MR signal for other spatial frequencies.

MRI is a time consuming procedure, and thus acceleration of MR image acquisition is critical. An MR signal is sampled in a spectral space which represents a 2D Fourier transform of an MR image. If samples are acquired sequentially, a total acquisition time may depend on the number of samples. Thus, one approach to accelerating the acquisition of an MR image is to thin out sampling frequencies and reconstruct the MR image only from measured frequencies.

The present disclosure provides a method of reconstructing an MR image from an undersampled k-space at a high speed. A method of generating an MR image (or a method of reconstructing an MR image) requires an undersampled k-space and a sampling mask, which is a binary matrix, where "1" means that a certain frequency (a point in k-space at a corresponding location) is sampled, and "0" means that the certain frequency (the point in k-space at the corresponding location) is not sampled. According to the method, a reconstructed image is generated and output.

According to an embodiment, the acquisition unit 110 may acquire an undersampled spectrum in a k-space, which corresponds to some spatial frequencies, and thus, data acquisition time may be shortened.

The reconstruction unit 120 may generate a target image based on the undersampled spectrum.

In detail, as described above, the reconstruction unit 120 may include the first sub-reconstruction unit 130, the second sub-reconstruction unit 140, and the image processor 150.

The first sub-reconstruction unit 130 may perform initial reconstruction that will be described with reference to operation 102 of FIG. 2. The first sub-reconstruction unit 130 may perform the initial reconstruction by using a Split Bregman algorithm as will be described with reference to FIG. 3 or approximate sparse coding as will be described with reference to FIG. 4.

The first sub-reconstruction unit 130 may perform the initial reconstruction on data corresponding to unsampled positions in the k-space by using the Split Bregman algorithm or approximate sparse coding as will be described in more detail below.

The second sub-reconstruction unit 140 may perform multiband decomposition that will be described with reference to operation 103 of FIG. 2. Furthermore, the second sub-reconstruction unit 140 may perform dictionary learning reconstruction that will be described with reference to operation 104 of FIG. 2 and FIG. 5.

The second sub-reconstruction unit 140 may decompose the initially reconstructed spectrum in k-space into multiple bands to thereby generate a plurality of individual spectra respectively corresponding to the multiple bands.

Furthermore, the second sub-reconstruction unit 140 may perform dictionary learning reconstruction on images corresponding to the decomposed multiple bands. For example, the second sub-reconstruction unit 140 may perform the dictionary learning reconstruction by alternating sparse approximation and reconstructing of measured frequencies.

The image processor 150 may generate a target image by merging together reconstructed images corresponding to different frequency bands. The image processor 150 may receive reconstructed images respectively corresponding to frequency bands decomposed by the second sub-reconstruction unit 140 and merge the reconstructed images together to thereby generate a target image. The image processor 150 may transmit the target image to a display (not shown).

An MRI apparatus according to an embodiment combines high performance and fast convergence characteristics provided by a Split Bregman iterative algorithm with the advantages of dictionary learning. Operations of the MRI apparatus will now be described in detail.

Figure 2:
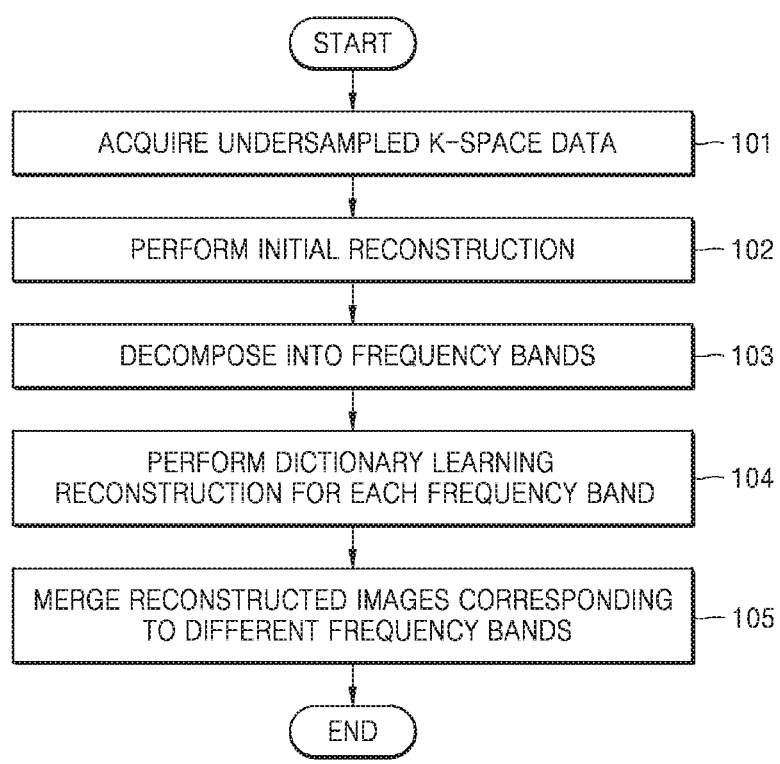
FIG. 2 is a flowchart of a method of reconstructing an MR image at a high speed, according to an embodiment.

FIG. 2 is a flowchart of a method of reconstructing an MR image at a high speed, according to an embodiment.

Referring to FIG. 2, an MRI apparatus may acquire undersampled k-space data (operation 101). For example, the MRI apparatus may acquire spectral data in k-space via a receiver coil according to a sampling scheme defined by a sampling mask forming an undersampling spectrum to be processed.

The MRI apparatus may perform initial reconstruction (operation 102). For example, the MRI apparatus may perform the initial reconstruction by filling empty (unsampled) positions in the k-space with an initial guess.

The MRI apparatus may decompose an initialized spectrum into a plurality of frequency bands (operation 103). The MRI apparatus may decompose the initialized spectrum (initially reconstructed spectrum) in the k-space into frequency bands to thereby produce a plurality of individual spectra respectively corresponding to the frequency bands.

The MRI apparatus may perform dictionary learning reconstruction for each frequency band (operation 104). For example, the MRI apparatus may reconstruct each of the produced individual spectra by using a dictionary learning compressive sensing algorithm.

The MRI apparatus may merge the reconstructed images corresponding to different frequency bands (operation 105). For example, the MRI apparatus may merge together all reconstructed images corresponding to different frequency bands by using a sum operator and generate a final reconstruction result, i.e., a full spectrum in the k-space corresponding to a deblurred and denoised MR signal.

In the above-described method, a learning-based approach is used to create a dictionary used for image reconstruction. The dictionary is learned in advance based on a set of fully-sampled training MR images.

The operations of the method will now be described in more detail.

Initial Reconstruction

A naive object reconstruction means an inverse Fourier transform of undersampled spectral data with no preprocessing. However, such reconstruction is strongly corrupted by aliasing effects due to zeros in measurements, especially in the case of regular undersampling. A straightforward way is to fill empty samples in the Fourier domain with some non-zero values to avoid aliasing and help reconstruction algorithm for fast convergence. This procedure is called initialization or initial reconstruction.

There are many approaches to taking initial data, i.e., a constant value, varying gradient (slope), or random complex values. The empty samples may be obtained from the Fourier spectrum of a somehow preprocessed aliased object in the image domain, e.g., by regularized deconvolution using the Split Bregman iterative algorithm or approximate sparse coding, deblurring reconstructed by using some sophisticated method as blind deconvolution, denoising, smoothing, and sharpening. This may essentially suppress aliasing effects and significantly increase both convergence rate and reconstruction quality. Furthermore, some prior information about the object, an object model or a data acquisition model may be used.

According to an embodiment, the Split Bregman algorithm [T. Goldstein, and S. Osher, "The Split Bregman method for l1-regularized problems," SIAM J. on Imag. Sciences 2, 323-343 (2009)] may be used in operation 102 (initialization). This algorithm provides the efficiency and fast convergence rate for the method according to the embodiment.

As noted in [D. L. Donoho, "Compressed sensing," IEEE Trans. Inf. Theory 52, 1289-1306 (2006)], a CS reconstruction problem is initially simplified and reformulated as the following basis pursuit denoising problem:

$$x = \operatorname*{argmin}_{x} \|F_u(x) - y\|_2^2 + \lambda \cdot \|\Psi(x)\|_1 \quad (1)$$

Equation (1) is related to general CS and defines a result derived from a convex cost function to be minimized. Here, x is a vector of an object image to be reconstructed, $F_u$ is a partially sampling Fourier transform, y is a vector of the measured undersampled spectrum, $\Psi$ is a sparsifying transform, $\lambda$ is a regularization parameter, $l_1$ norm $\|\ldots\|_1$ is defined as a sum of absolute values of elements of the vector, and $l_2$ norm $\|\ldots\|_2$ is defined as the square-root of the sum of squares of the elements of the vector.

The $l_1$ and $l_2$ norms in accordance with [Y. Wang et al., "A fast algorithm for image deblurring with total variation regularization," CAAM Technical Report (2007)] may be decoupled as:

$$\min_{x,d} \|F_u(x) - y\|_2^2 + \lambda \cdot \|d\|_1 + \mu \cdot \|\Psi(x) - d\|_2^2 \quad (2)$$

where d is a sparse object approximation. Furthermore, d is an approximate value of x. Thus, it follows the Split Bregman iterative algorithm:

$$x^{k+1} = \arg\min_{x} \|F_u(x) - y\|_2^2 + \mu \cdot \|d^k - \Psi(x) - b^k\|_2^2 \quad (3.1)$$

$$d^{k+1} = \arg\min_{d} \lambda \cdot \|d\|_1 + \mu \cdot \|d - \Psi(x^{k+1}) - b^k\|_2^2 \quad (3.2)$$

$$b^{k+1} = b^k + (\Psi(x^{k+1}) - d^{k+1}) \quad (3.3)$$

where $\mu$ is a regularization parameter and $b^k$ is an update of the Bregman parameters.

Figure 3:
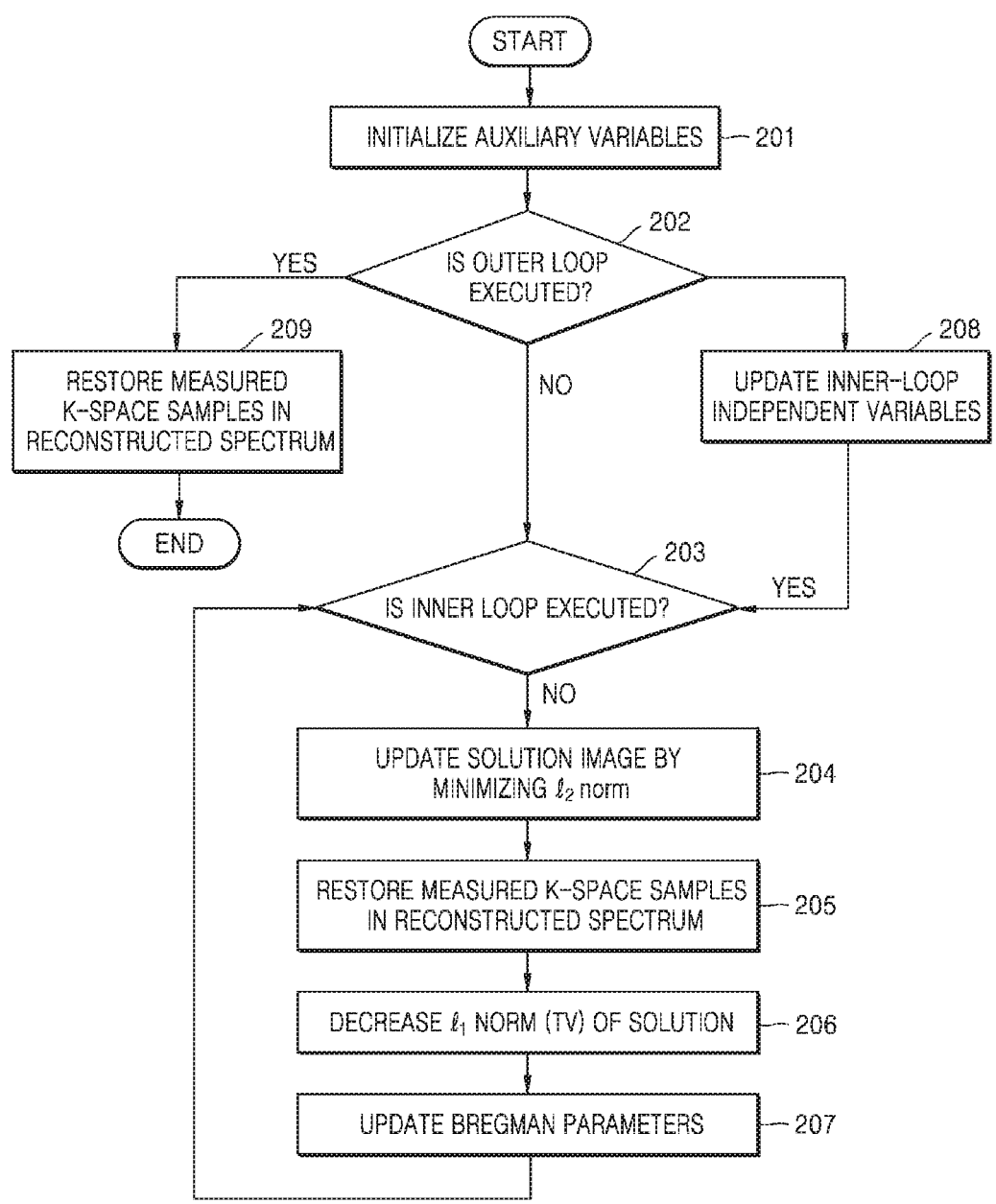
FIG. 3 is a detailed flowchart for explaining initialization based on a Split Bregman method, according to an embodiment.

FIG. 3 is a flowchart of a Split Bregman initialization algorithm. As described in [T. Goldstein, and S. Osher, "The Split Bregman method for $l_1$-regularized problems," SIAM J. on Imag. Sciences 2, 323-343 (2009)], the algorithm comprises two nested loops.

Referring to FIG. 3, an MRI apparatus may initialize auxiliary variables (operation 201). For example, the MRI apparatus may initialize auxiliary variables of sparse object approximation $d^0$ and Bregman parameter $b^0$ with zero vectors.

The MRI apparatus may determine whether an outer loop is executed (operation 202). In other words, the MRI apparatus may determine whether the outer loop is completed. If the outer loop is not executed, the algorithm may proceed to operation 203. Otherwise, if the outer loop is executed, the MRI apparatus may perform operation 209.

The MRI apparatus may determine whether an inner loop is executed (operation 203). In other words, the MRI apparatus may determine whether the inner loop is completed. If the inner loop is not executed, the algorithm may proceed to the inner loop. Otherwise, if the inner loop is executed, the MRI apparatus may perform operation 208.

The MRI apparatus may update a solution image by minimizing a $l_2$ norm (operation 204). The MRI apparatus may reconstruct measured k-space samples in a reconstructed spectrum (operation 205). The MRI apparatus may then shrink a $l_1$ norm (total variation (TV)) of a solution (operation 206). The MRI apparatus may update Bregman parameters (operation 207).

For example, in the inner loop, the above-described Split Bregman routines <Equation (3.1) through Equation (3.3)> may be performed, and the inner loop may include:

recalculating a target object estimate $x^{k+1}$ by optimizing the $l_2$ norm (operation 204);

recomputing the sparse object approximation $d^{k+1}$ by solving a $l_1$-regularized problem (operation 205); and updating Bregman parameters $b^{k+1}$ (operation 207).

Optimization with respect to the l1 norm may be realized via soft thresholding with a threshold that is equal to ½µ (operation 206).

In order to increase the reconstruction accuracy and reduce the number of iterations, the reconstructed object may be additionally updated by reconstructing the measured k-space samples in the reconstructed Fourier spectrum of the target object estimate $x^{k+1}$ (operation 205).

The MRI apparatus may update auxiliary inner-loop independent variables that are used to recompute the object estimate (operation 208).

After performing operation 208, the algorithm may return to operation 202.

As described above, if the outer loop is completed (operation 202), the algorithm proceeds to operation 209, where the reconstructed object is updated again by reconstructing the measured k-space samples in the reconstructed Fourier spectrum. Thereafter, the Split Bregman based initialization algorithm is completed.

A differential operator may be used as a sparsifying transform $\Psi$. In this case, total variation regularization is generally applied for image reconstruction.

Approximate Sparse Coding for Computing Initial Guess

In an embodiment, an initial guess may be computed using an approximate sparse coding method during the initialization (operation 102 of FIG. 2). The main idea of the approximate sparse coding method is to use trainable models to predict sparse codes with fewer computations than actually needed by exact algorithms. As one of the variants of a trainable model for a sparse code prediction, a Learned Coordinate Descent algorithm (LCoD) may be used. For example, LCoD architectures may be as described in [Karol Gregor and Yann LeCun, Learning Fast Approximations of Sparse Coding, ICML 2010].

Figure 4:
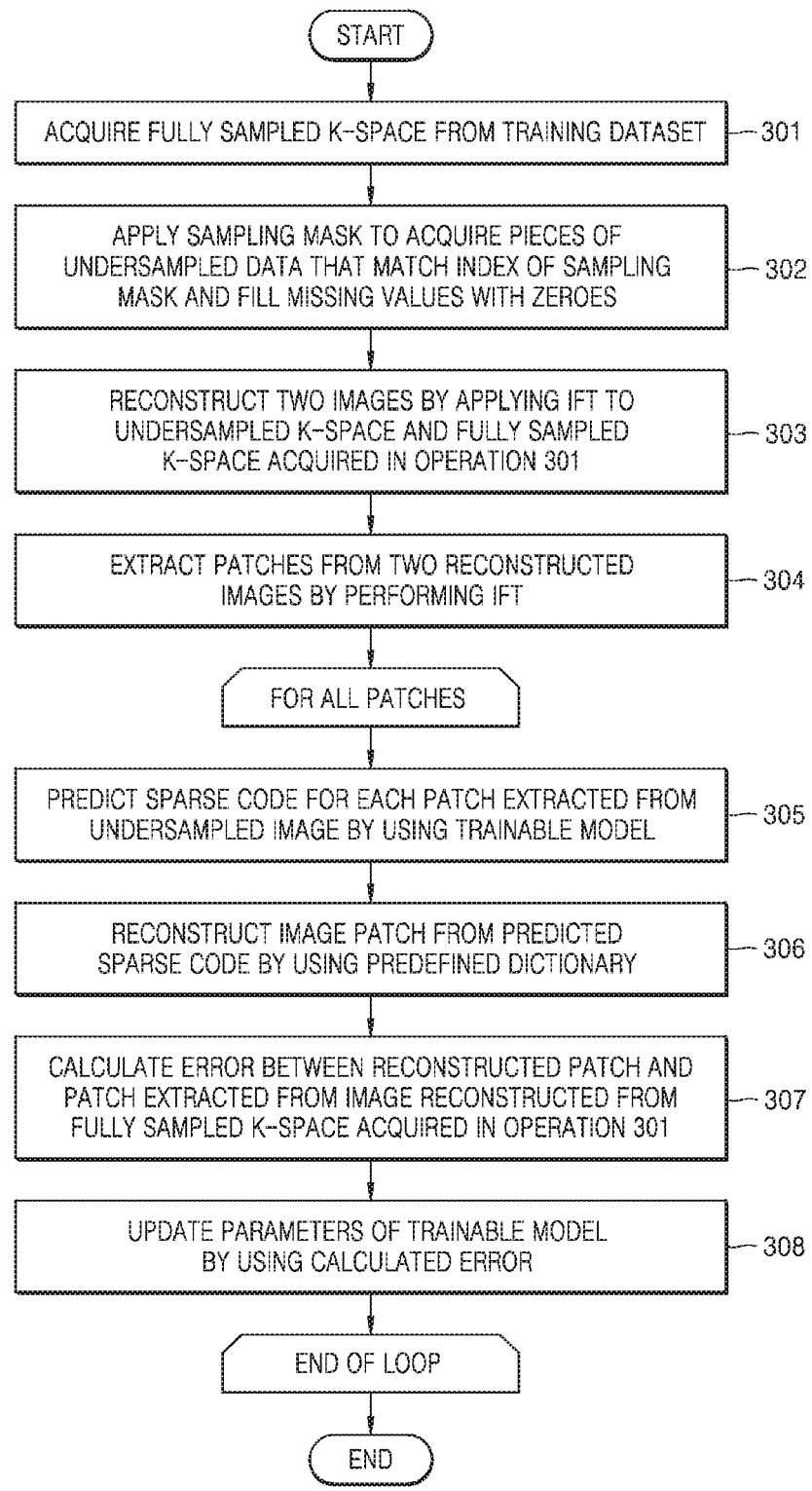
FIG. 4 is a flowchart of an approximate sparse coding method according to an embodiment.

FIG. 4 is a flowchart of an algorithm of model training for a sparse code prediction.

In order to train a model sparse coding dictionary, a training set and a sampling mask are to be predefined. The training set has to contain fully sampled data.

Referring to FIG. 4, an MRI apparatus may acquire a fully sampled k-space from a training dataset (operation 301). For example, the fully sampled k-space may be fetched from the training dataset.

The MRI apparatus may apply a sampling mask to acquire pieces of undersampled data that match an index of the sampling mask and fill missing values with zeroes (operation 302). For example, in operation 302, a predefined sampling mask may be applied to the k-space to acquire an undersampled k-space in which missing values are filled with zeroes.

The MRI apparatus may reconstruct two images by applying an inverse Fourier transform to the undersampled k-space and the fully sampled k-space acquired in operation 301 (operation 303). For example, in operation 303, the two images may be reconstructed by applying an inverse Fourier transform: one from the undersampled k-space (with artifacts due to zero filling) and another from the fully sampled k-space. Small image patches are extracted from both of these two images The MRI apparatus may extract patches from the two reconstructed images by performing an inverse Fourier transform (operation 304). The MRI apparatus may reconstruct two images by applying the inverse Fourier transform to the undersampled and fully sampled k-spaces. For example, in operation 304, small image patches may be extracted from both images. The size of each of the extracted patches is equal to that of a dictionary element.

A loop, i.e., operations 305 through 308, is run for all the patches.

The MRI apparatus may predict a sparse code for each of the patches extracted from an undersampled image by using a trainable model (operation 305). In other words, in operation 305, the sparse code may be predicted by using the trainable model.

The MRI apparatus may reconstruct an image patch from the predicted sparse code by using a predefined dictionary (operation 306). For example, in operation 306, the image patch may be reconstructed using the predicted sparse code and the predefined dictionary.

The MRI apparatus may calculate an error between the reconstructed image patch and the patch extracted from the image reconstructed from the fully sampled k-space acquired in operation 301 (operation 307). For example, in operation 307, the reconstructed image patch is used to compute an error by being compared with a patch extracted from a fully sampled image.

The MRI apparatus may update parameters of the trainable model by using the calculated error (operation 308). For example, in operation 308, the parameters of the trainable model may be updated by using a certain optimization method such as a gradient descent method. This process is repeated until a training process converges.

Dictionary Learning

Referring back to FIG. 2, operation 104 is based on sparse approximation of an input signal using a learned dictionary.

In operation 104, an optimization equation defined by the following Equation (4) is used:

$$x = \arg \min_x \|F_u(x) - y\|_2^2 + \lambda \|\Psi(x)\|_0 \qquad (4)$$

where $l_0$ norm $\|\ldots\|_0$ is defined as a number of non-zero elements of a vector.

In a dictionary learning approach, a sparsifying transform is represented by sparse decomposition of an input to basis elements from a dictionary. A solution of the optimization equation shown in Equation (4) is obtained by an iterative algorithm including operations 401 through 408 illustrated in FIG. 5.

Figure 5:
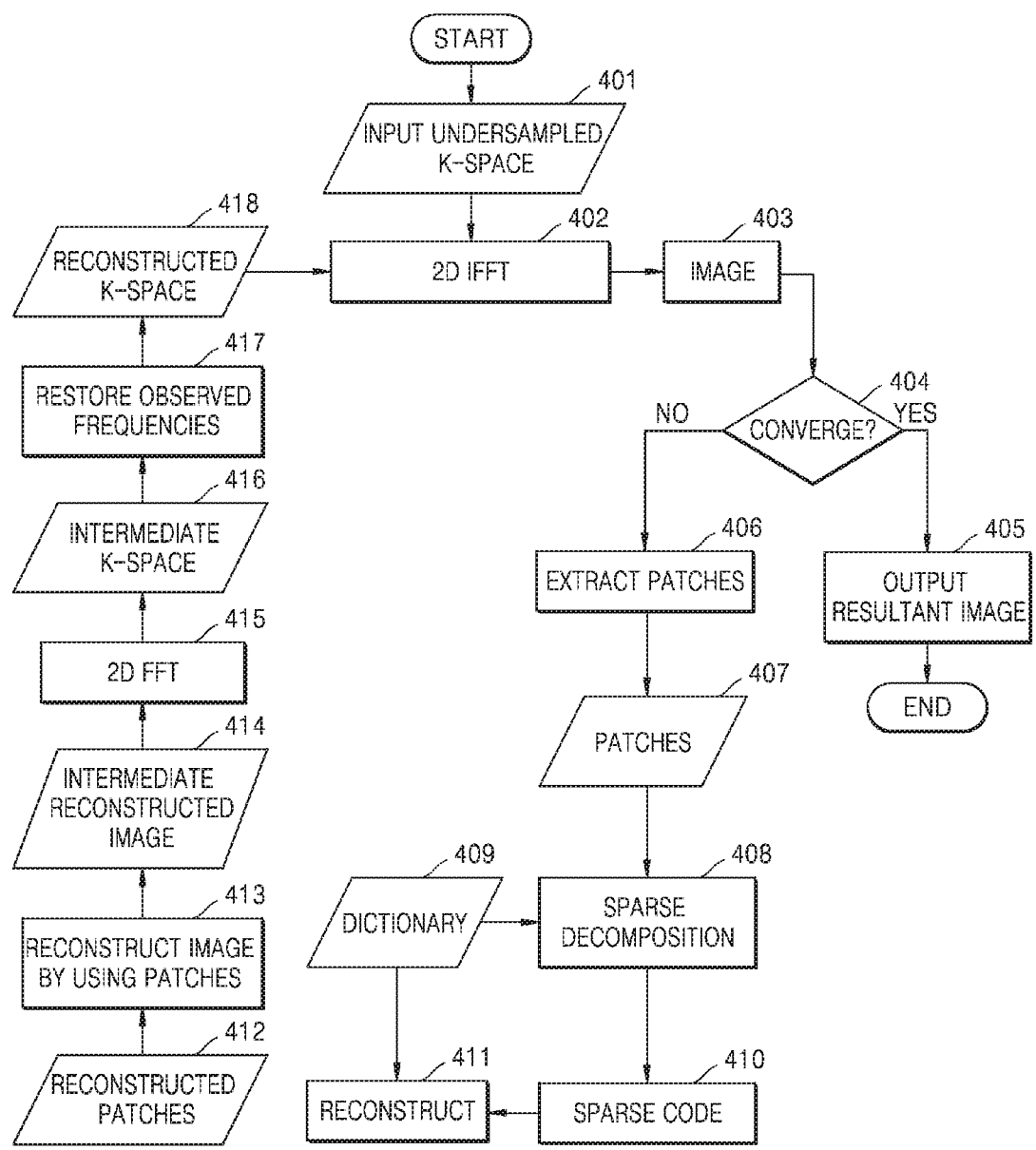
FIG. 5 is a flowchart of a reconstruction method based on dictionary learning according to an embodiment.

Referring to FIG. 5, an MRI apparatus obtains an image 403 by applying an inverse Fourier transform (operation 402) to an input undersampled k-space (operation 401). Then, until a solution converges (operation 404), the following operations are performed. A set of overlapping patches 407 are extracted from the image 403 (operation 406). Thereafter, sparse decomposition is performed on each of the extracted patches 407 (operation 408). In operation 408, an optimization equation defined by the following Equation (5) is used:

$$z = \arg \min_z \|X - Dz\|_F^2 + \delta \|z\|_0 \qquad (5)$$

where columns of X are vectorized patches, columns of z are sparse code vectors, D is a dictionary transform matrix, and δ is a regularization parameter.

In the above-described problem, elements of a dictionary 409 are represented as columns of the dictionary transform matrix D, and each column of X aims to be represented as a linear combination of the dictionary elements with only a small number of non-zero elements (thus, columns of z are sparse). This problem may be resolved by a greedy Orthogonal Matching Pursuit algorithm.

A sparse code z 410 is obtained for each patch, and reconstructed patches 412 are calculated as a linear combination of the dictionary elements with sparse codes obtained as coefficients. Then, an intermediate reconstructed image 414 is obtained by merging the reconstructed patches 412 with overlaps (operation 413). Next, the intermediate reconstructed image 414 is transformed back into a frequency space by applying a fast Fourier transform (operation 415), and intermediate k-space data is acquired (operation 416).

Then, observed frequencies are reconstructed in an intermediate k-space (operation 416) by the measured data (operation 417). A k-space 418 with the reconstructed observed frequencies is transformed to an image space by the inverse Fourier transform (operation 402). If the solution converges in operation 404, the image 403 is output as a result of the reconstruction (operation 405). Otherwise, if the solution does not converge, a new iteration begins.

Non-Uniform Sized Patches

The method according to an embodiment is performed by using various sampling techniques. As a result of the procedure of extracting patches from an input image, a set of quadrangular pieces of the image is produced. Optimal aspect ratio (a proportion of width relative to height) of a patch depends on a k-space sampling scheme. A common way of sampling in an MRI apparatus is to acquire phase-encoding lines that represent rows in a k-space.

Thus, information about frequencies is lost along a y-direction (vertical coordinate). These losses affect an image (obtained from an undersampled k-space) in vertical aliasing artifacts. If the number of dictionary elements is fixed, the size of a patch shouldn't be very large in both dimensions because it is difficult to encode such amount of information with only a small number of dictionary elements.

When a fixed amount of information (a fixed number of pixels) within a patch is used, it may be more optimal to cover more data along a vertical direction using a single patch. This is applicable because aliasing artifacts caused by skipping phase-encoding lines are distributed along the vertical direction due to a Cartesian sampling scheme. Such covering strategy with a fixed amount of information per patch may be performed by applying non-uniform sized quadrangular patches.

For example, the non-uniform sized quadrangular patches may be applied by increasing a patch height while decreasing a patch width. Non-square, rectangular patches may achieve better reconstruction quality than square patches. In this case, the number of pixels in a rectangular patch is less than or equal to the number of pixels in a square patch.

For non-Cartesian isotropic random sampling scheme, use of square patches may achieve higher reconstruction quality than use of a rectangular patch. In a general case, an aspect ratio of a patch relies on a proportion of lost information along the x- and y-directions (amount of anisotropy).

Multiband Decomposition

In the method according to an embodiment, one approach to exploiting a multilevel structure of data is to reconstruct a plurality of image components corresponding to multiple frequency bands (operation 103 of FIG. 2). In the method, the initially reconstructed spectrum (obtained in operation 102) is decomposed into frequency bands corresponding to a group of several partial bands.

For example, the initially reconstructed spectrum may be decomposed into frequency bands corresponding to a group of low, intermediate, and high frequency bands.

After the decomposition, several new (decomposed) k-spaces are created, each of which contains only frequencies within its corresponding band, while the other frequencies are filled with zeros and marked as measured. Decomposition of an MR signal into frequency bands yields shrinkage of signal variety within a band (a signal has a simple form in each band), thus consequently increasing a sparsity of the signal and a quality of final reconstruction.

Such truncated k-spaces are treated as inputs to a main loop of dictionary learning reconstruction (operation 104 of FIG. 2) and are processed in parallel. After images respectively corresponding to bands are reconstructed, a final reconstructed image is obtained by summing up the reconstructed images corresponding to all bands (operation 105 of FIG. 2). During the dictionary learning, each training image is decomposed into frequency bands in the same way, and a unique dictionary is separately learned for each of the frequency bands.

In the reconstruction operation, each band is reconstructed using its corresponding dictionary. If all frequencies in the current band are measured, the reconstruction of the band is performed by simply applying an inverse Fourier transform. Selection of a shape of a band depends on the type of a sampling scheme.

For example, for Cartesian one-dimensional sampling, bands have the shape of rectangular stripes in a k-space, which are aligned with sampling lines. For radial-symmetric or isotropic random sampling, bands are represented as concentric rings centered around a zero frequency.

System for Reconstructing MR Image from Undersampled Data

Figure 6:
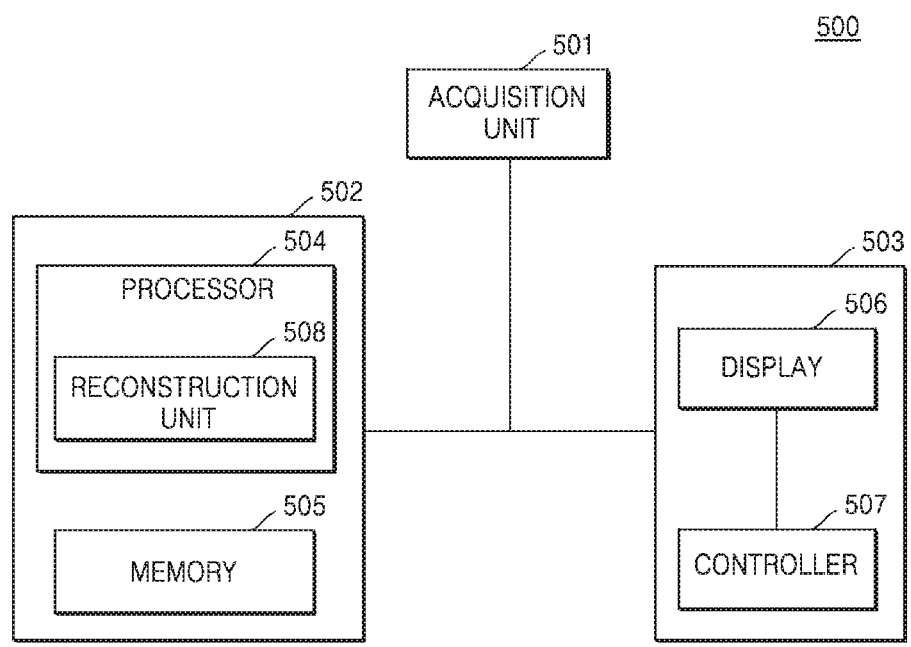
FIG. 6 illustrates a system in which embodiments may be implemented.

FIG. 6 is a diagram for explaining an MRI system 500 according to an embodiment.

Referring to FIG. 6, the MRI system 500 may include an acquisition unit 501, a reconstruction server 502, and an operator console 503.

The acquisition unit 501 may acquire an undersampled k-space. For example, the acquisition unit 501 may acquire spectral data in a k-space via a receiver coil according to a sampling scheme defined by a sampling mask. The acquisition unit 501 may be implemented using separate medical equipment that is distinguished from the reconstruction server 502 or the operator console 503.

The reconstruction server 502 may include a processor 504 and a memory 505. The processor 504 may include a reconstruction unit 508.

According to an embodiment, the reconstruction unit 508 may reconstruct undersampled MRI data. The reconstruction unit 508 may perform the initial reconstruction by filling empty (unsampled) positions in the k-space with an initial guess. The reconstruction unit 508 may also decompose an initialized spectrum in the k-space into frequency bands and generate a plurality of individual spectra respectively corresponding to the frequency bands. The reconstruction unit 508 may reconstruct each of the plurality of individual spectra by using a dictionary learning compressive sensing algorithm.

The reconstruction unit 508 may merge together all reconstructed images corresponding to different frequency bands by using a sum operator and generate a final reconstruction result, i.e., a full spectrum in the k-space corresponding to a deblurred and denoised MR signal.

The processor 504 may perform various operations, other than those of the reconstruction unit 508, for implementing embodiments.

The memory 505 may store a file having k-space data in the undersampled k-space acquired by the acquisition unit 501.

The operator console 503 may include a display 506 and a controller 507.

The controller 507 may run a program for performing image reconstruction. A result of running the program may be output by the display 506.

Thus, the MRI apparatus 500 according to the present embodiment may acquire k-space data in a shorter time.

Figure 7:
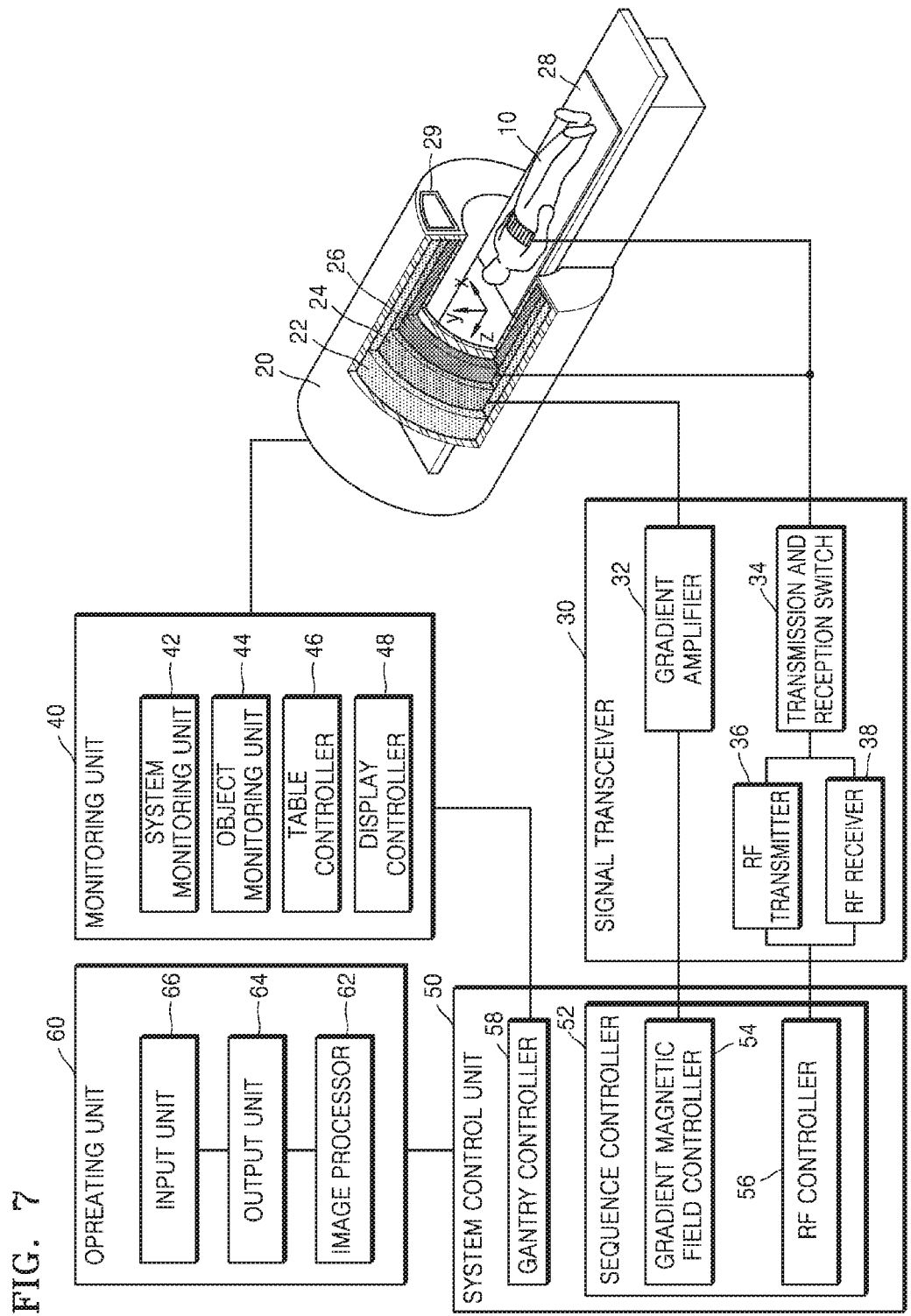
FIG. 7 illustrates an MRI system according to an embodiment.

FIG. 7 illustrates an MRI system according to an embodiment. Referring to FIG. 1, the general MRI system may include a gantry 20, a signal transceiver 30, a monitoring unit 40, a system control unit 50, and an operating unit 60.

The gantry 20 prevents external emission of electromagnetic waves generated by a main magnet 22, a gradient coil 24, and an RF coil 26. A magnetostatic field and a gradient magnetic field are formed in a bore in the gantry 20, and an RF signal is emitted toward an object 10.

The main magnet 22, the gradient coil 24, and the RF coil 26 may be arranged in a predetermined direction of the gantry 20. The predetermined direction may be a coaxial cylinder direction. The object 10 may be disposed on a table 28 that is capable of being inserted into a cylinder along a horizontal axis of the cylinder.

The main magnet 22 generates a magnetostatic field or a static magnetic field for aligning magnetic dipole moments of atomic nuclei of the object 10 in a constant direction. A precise and accurate MR image of the object 10 may be obtained due to a magnetic field generated by the main magnet 22 being strong and uniform.

The gradient coil 24 includes X, Y, and Z coils for generating gradient magnetic fields in X-, Y-, and Z-axis directions crossing each other at right angles. The gradient coil 24 may provide location information of each region of the object 10 by differently inducing resonance frequencies according to the regions of the object 10.

The RF coil 26 may emit an RF signal toward a patient and receive an MR signal emitted from the patient. In detail, the RF coil 26 may transmit, toward atomic nuclei included in the patient and having precessional motion, an RF signal having the same frequency as that of the precessional motion, stop transmitting the RF signal, and then receive an MR signal emitted from the atomic nuclei included in the patient.

For example, in order to transit an atomic nucleus from a low energy state to a high energy state, the RF coil 26 may generate and apply an electromagnetic wave signal that is an RF signal corresponding to a type of the atomic nucleus, to the object 10. When the electromagnetic wave signal generated by the RF coil 26 is applied to the atomic nucleus, the atomic nucleus may transit from the low energy state to the high energy state. Then, when electromagnetic waves generated by the RF coil 26 disappear, the atomic nucleus to which the electromagnetic waves were applied transits from the high energy state to the low energy state, thereby emitting electromagnetic waves having a Lamor frequency. In other words, when the applying of the electromagnetic wave signal to the atomic nucleus is stopped, an energy level of the atomic nucleus is changed from a high energy level to a low energy level, and thus the atomic nucleus may emit electromagnetic waves having a Lamor frequency. The RF coil 26 may receive electromagnetic wave signals from atomic nuclei included in the object 10.

The RF coil 26 may be realized as one RF transmitting and receiving coil having both a function of generating electromagnetic waves each having an RF that corresponds to a type of an atomic nucleus and a function of receiving electromagnetic waves emitted from an atomic nucleus. Alternatively, the RF coil 26 may be realized as a transmission RF coil having a function of generating electromagnetic waves each having an RF that corresponds to a type of an atomic nucleus, and a reception RF coil having a function of receiving electromagnetic waves emitted from an atomic nucleus.

The RF coil 26 may be fixed to the gantry 20 or may be detachable. When the RF coil 26 is detachable, the RF coil 26 may be an RF coil for a part of the object, such as a head RF coil, a chest RF coil, a leg RF coil, a neck RF coil, a shoulder RF coil, a wrist RF coil, or an ankle RF coil.

The RF coil 26 may communicate with an external apparatus via wires and/or wirelessly, and may also perform dual tune communication according to a communication frequency band.

The RF coil 26 may be a birdcage coil, a surface coil, or a transverse electromagnetic (TEM) coil according to structures.

The RF coil 26 may be a transmission exclusive coil, a reception exclusive coil, or a transmission and reception coil according to methods of transmitting and receiving an RF signal.

The RF coil 26 may be an RF coil having various numbers of channels, such as 16 channels, 32 channels, 72 channels, and 144 channels.

The gantry 20 may further include a display 29 disposed outside the gantry 20 and a display (not shown) disposed inside the gantry 20. The gantry 20 may provide predetermined information to the user or the object 10 through the display 29 and the display respectively disposed outside and inside the gantry 20.

The signal transceiver 30 may control the gradient magnetic field formed inside the gantry 20, i.e., in the bore, according to a predetermined MR sequence, and control transmission and reception of an RF signal and an MR signal.

The signal transceiver 30 may include a gradient amplifier 32, a transmission and reception switch 34, an RF transmitter 36, and an RF receiver 38.

The gradient amplifier 32 drives the gradient coil 24 included in the gantry 20, and may supply a pulse signal for generating a gradient magnetic field to the gradient coil 24 under the control of a gradient magnetic field controller 54. By controlling the pulse signal supplied from the gradient amplifier 32 to the gradient coil 24, gradient magnetic fields in X-, Y-, and Z-axis directions may be synthesized.

The RF transmitter 36 and the RF receiver 38 may drive the RF coil 26. The RF transmitter 36 may supply an RF pulse in a Lamor frequency to the RF coil 26, and the RF receiver 38 may receive an MR signal received by the RF coil 26.

According to an embodiment, the RF receiver 38 including the acquisition unit 110 of FIG. 1 may acquire an undersampled spectrum in k-space via the acquisition unit 110. Since the acquisition unit 110 acquires the undersampled spectrum in the k-space corresponding to some spatial frequencies, a data acquisition time may be shortened.

The transmission and reception switch 34 may adjust transmitting and receiving directions of the RF signal and the MR signal. For example, the transmission and reception switch 34 may emit the RF signal toward the object 10 through the RF coil 26 during a transmission mode, and receive the MR signal from the object 10 through the RF coil 26 during a reception mode. The transmission and reception switch 34 may be controlled by a control signal output by an RF controller 56.

The monitoring unit 40 may monitor or control the gantry 20 or devices mounted on the gantry 20. The monitoring unit 40 may include a system monitoring unit 42, an object monitoring unit 44, a table controller 46, and a display controller 48.

The system monitoring unit 42 may monitor and control a state of the magnetostatic field, a state of the gradient magnetic field, a state of the RF signal, a state of the RF coil 26, a state of the table 28, a state of a device measuring body information of the object 10, a power supply state, a state of a thermal exchanger, and a state of a compressor.

The object monitoring unit 44 monitors a state of the object 10. In detail, the object monitoring unit 44 may include a camera for observing a movement or position of the object 10, a respiration measurer for measuring the respiration of the object 10, an electrocardiogram (ECG)

measurer for measuring the electrical activity of the object 10, or a temperature measurer for measuring a temperature of the object 10.

The table controller 46 controls a movement of the table 28 where the object 10 is positioned. The table controller 46 may control the movement of the table 28 according to a sequence control of a sequence controller 50. For example, during moving imaging of the object 10, the table controller 46 may continuously or discontinuously move the table 28 according to the sequence control of the sequence controller 50, and thus the object 10 may be photographed in a field of view (FOV) larger than that of the gantry 20.

The display controller 48 controls the display 29 disposed outside the gantry 20 and the display disposed inside the gantry 20. In detail, the display controller 48 may control the display 29 and the display to be on or off, and may control a screen image to be output on the display 29 and the display. Also, when a speaker is located inside or outside the gantry 20, the display controller 48 may control the speaker to be on or off, or may control sound to be output via the speaker.

The system control unit 50 may include the sequence controller 52 for controlling a sequence of signals formed in the gantry 20, and a gantry controller 58 for controlling the gantry 20 and the devices mounted on the gantry 20.

The sequence controller 52 may include the gradient magnetic field controller 54 for controlling the gradient amplifier 32, and the RF controller 56 for controlling the RF transmitter 36, the RF receiver 38, and the transmission and reception switch 34. The sequence controller 52 may control the gradient amplifier 32, the RF transmitter 36, the RF receiver 38, and the transmission and reception switch 34 according to a pulse sequence received from the operating unit 60. Here, the pulse sequence includes all information required to control the gradient amplifier 32, the RF transmitter 36, the RF receiver 38, and the transmission and reception switch 34. For example, the pulse sequence may include information about a strength, an application time, and application timing of a pulse signal applied to the gradient coil 24.

The operating unit 60 may request the system control unit 50 to transmit pulse sequence information while controlling an overall operation of the MRI system.

The operating unit 60 may include an image processor 62 for receiving and processing the MR signal received by the RF receiver 38, an output unit 64, and an input unit 66.

The image processor 62 may process the MR signal received from the RF receiver 38 so as to generate MR image data of the object 10.

The image processor 62 receives the MR signal received by the RF receiver 38 and performs any one of various signal processes, such as amplification, frequency transformation, phase detection, low frequency amplification, and filtering, on the received MR signal.

The image processor 62 may arrange digital data in a k space (for example, also referred to as a Fourier space or a frequency space) of a memory, and rearrange the digital data into image data via 2D or 3D Fourier transformation.

If needed, the image processor 62 may perform a composition process or difference calculation process on the image data. The composition process may include an addition process on a pixel or a maximum intensity projection (MIP) process. The image processor 62 may store not only the rearranged image data but also image data on which a composition process or a difference calculation process is performed, in a memory (not shown) or an external server.

The image processor 62 may perform any of the signal processes on the MR signal in parallel. For example, the image processor 62 may perform a signal process on a plurality of MR signals received by a multi-channel RF coil in parallel so as to rearrange the plurality of MR signals into image data.

According to an embodiment, the image processor 62 may include the reconstruction unit 120 of FIG. 1 and generate a target image based on the undersampled spectrum. Furthermore, as described with reference to FIG. 1, the reconstruction unit 120 may include the first sub-reconstruction unit 130, the second sub-reconstruction unit 140, and the image processor 150.

The first sub-reconstruction unit 130 may perform initial reconstruction on data corresponding to unsampled positions in the k-space by using the Split Bregman algorithm or approximate sparse coding.

The second sub-reconstruction unit 140 may decompose the initially reconstructed spectrum in k-space into multiple bands and generate a plurality of individual spectra respectively corresponding to the multiple bands.

Furthermore, the second sub-reconstruction unit 140 may perform dictionary learning reconstruction on images corresponding to the decomposed multiple bands.

Thus, the image processor 62 may obtain an MR image at a high speed.

The output unit 64 may output image data generated or rearranged by the image processor 62 to the user. The output unit 64 may also output information required for the user to manipulate the MRI system, such as a user interface (UI), user information, or object information. The output unit 64 may be a speaker, a printer, a cathode-ray tube (CRT) display, a liquid crystal display (LCD), a plasma display panel (PDP), an organic light-emitting device (OLED) display, a field emission display (FED), a light-emitting diode (LED) display, a vacuum fluorescent display (VFD), a digital light processing (DLP) display, a flat panel display (FPD), a 3-dimensional (3D) display, or a transparent display.

The user may input object information, parameter information, a scan condition, a pulse sequence, or information about image composition or difference calculation by using the input unit 66. Examples of the input unit 66 may include a keyboard, a mouse, a trackball, a voice recognition unit, a gesture recognition unit, and a touch screen.

The signal transceiver 30, the monitoring unit 40, the system control unit 50, and the operating unit 60 are separate components in FIG. 10, but respective functions of the signal transceiver 30, the monitoring unit 40, the system control unit 50, and the operating unit 60 may be performed by another component. For example, the image processor 62 converts the MR signal received from the RF receiver 38 into a digital signal in FIG. 1, but alternatively, the conversion of the MR signal into the digital signal may be performed by the RF receiver 38 or the RF coil 26.

The gantry 20, the RF coil 26, the signal transceiver 30, the monitoring unit 40, the system control unit 50, and the operating unit 60 may be connected to each other by wire or wirelessly, and when they are connected wirelessly, the MRI system may further include an apparatus (not shown) for synchronizing clock signals therebetween. Communication between the gantry 20, the RF coil 26, the signal transceiver 30, the monitoring unit 40, the system control unit 50, and the operating unit 60 may be performed by using a high-speed digital interface, such as low voltage differential signaling (LVDS), asynchronous serial communication, such as a universal asynchronous receiver transmitter (UART), a low-delay network protocol, such as error synchronous serial communication or a controller area network (CAN), or optical communication.

Figure 8:
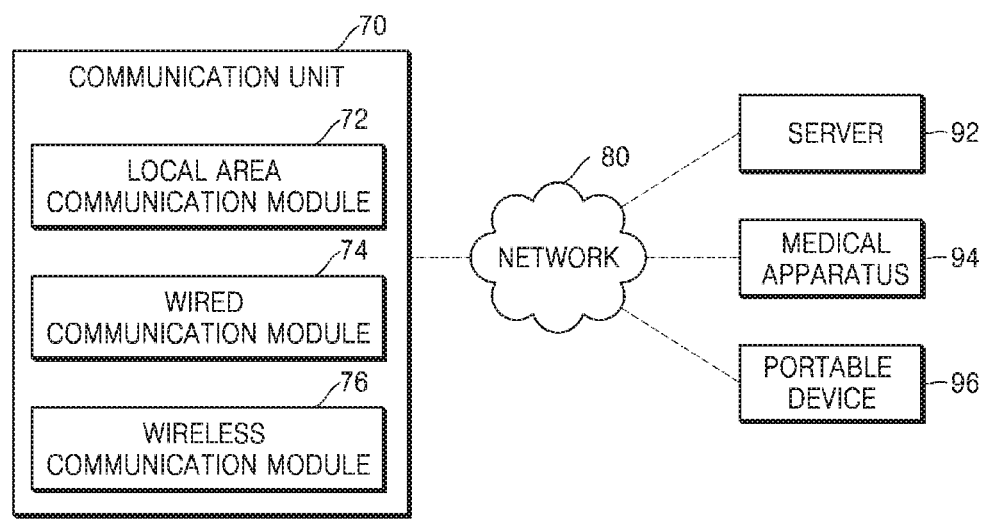
FIG. 8 illustrates an MRI system that performs communication via a communication unit according to an embodiment.

FIG. 8 illustrates an MRI system that performs communication via a communication unit 70 according to an embodiment.

Referring to FIG. 8, the communication unit 70 may be connected to at least one selected from the gantry 20, the signal transceiver 30, the monitoring unit 40, the system control unit 50, and the operating unit 60 of FIG. 7.

The communication unit 70 may transmit and receive data to and from a hospital server or another medical apparatus in a hospital, which is connected through a picture archiving and communication system (PACS), and perform data communication according to the digital imaging and communications in medicine (DICOM) standard.

As shown in FIG. 8, the communication unit 70 may be connected to a network 80 by wire or wirelessly to communicate with a server 92, a medical apparatus 94, or a portable device 96.

In detail, the communication unit 70 may transmit and receive data related to the diagnosis of an object through the network 80, and may also transmit and receive a medical image captured by the medical apparatus 94, such as a CT apparatus, an MRI apparatus, or an X-ray apparatus. In addition, the communication unit 70 may receive a diagnosis history or a treatment schedule of the object from the server 92 and use the same to diagnose the object. The communication unit 70 may perform data communication not only with the server 92 or the medical apparatus 94 in a hospital, but also with the portable device 96, such as a mobile phone, a personal digital assistant (PDA), or a laptop of a doctor or patient.

Also, the communication unit 70 may transmit information about a malfunction of the MRI system or about a medical image quality to a user through the network 80, and receive a feedback regarding the information from the user.

The communication unit 70 may include at least one component enabling communication with an external apparatus.

For example, the communication unit 70 may include a local area communication module 72, a wired communication module 74, and a wireless communication module 76. The local area communication module 72 refers to a module for performing local area communication with an apparatus within a predetermined distance. Examples of local area communication technology according to an embodiment of the present invention include, but are not limited to, a wireless local area network (LAN), Wi-Fi, Bluetooth, Zig-Bee, Wi-Fi direct (WFD), ultra wideband (UWB), infrared data association (IrDA), Bluetooth low energy (BLE), and near field communication (NFC).

The wired communication module 74 refers to a module for performing communication by using an electric signal or an optical signal. Examples of wired communication technology according to an embodiment of the present invention include wired communication techniques using a pair cable, a coaxial cable, and an optical fiber cable.

The wireless communication module 76 transmits and receives a wireless signal to and from at least one selected from a base station, an external apparatus, and a server in a mobile communication network. Here, the wireless signal may be a voice call signal, a video call signal, or data in any one of various formats according to transmission and reception of a text/multimedia message.

The above-described embodiments of the present disclosure may be written as computer programs and may be implemented in general-use digital computers that execute the programs using a computer-readable recording medium.

Examples of the computer-readable recording medium include magnetic storage media (e.g., ROM, floppy disks, hard disks, etc.), optical recording media (e.g., CD-ROMs, or DVDs), etc.

While one or more embodiments of the present invention have been described with reference to the figures, it will be understood by those of ordinary skill in the art that various changes in form and details may be made therein without departing from the spirit and scope of the present invention as defined by the following claims. Accordingly, the above embodiments and all aspects thereof are examples only and are not limiting.

What is claimed is:

1. A magnetic resonance imaging (MRI) apparatus comprising:
a memory; and
at least one processor configured to:
generate a target image based on an undersampled spectrum acquired in a k-space;
perform initial reconstruction on data corresponding to unsampled positions in the k-space by using a Split Bregman algorithm or approximate sparse coding to generate an initially reconstructed spectrum in the k-space;
decompose the initially reconstructed spectrum into multiple frequency bands to generate a plurality of individual spectra and perform dictionary learning reconstruction on images respectively corresponding to the decomposed multiple frequency bands by alternating sparse approximation and reconstructing of measured frequencies; and
generate a target image by merging together the reconstructed images respectively corresponding to the multiple frequency bands,
wherein the sparse approximation is performed based on rectangular overlapping patches extracted from an input image corresponding to an input magnetic resonance (MR) signal,
wherein the rectangular overlapping patches have a patch width smaller than a patch height, and an aspect ratio of the rectangular overlapping patches is determined based on a proportion of lost information along an x-axis direction and a y-axis direction.

2. The MRI apparatus of claim 1, wherein the at least one processor is further configured to perform the approximate sparse coding by collecting a fully sampled k-space dataset, applying a sampling mask, preparing undersampled data according to an index of the sampling mask, training a model to predict sparse codes for the undersampled data by using fully sampled data for calculation of an error, and predicting approximated sparse codes from the undersampled data by using the trained model.

3. The MRI apparatus of claim 1, wherein the sparse approximation further comprises extracting the rectangular overlapping patches, performing sparse decomposition of the extracted rectangular patches into sparse codes by using a dictionary, reconstructing the rectangular patches by using the sparse codes and the dictionary, and reconstructing an image by using the reconstructed patches.

4. The MRI apparatus of claim 1, wherein a dictionary used in the dictionary learning reconstruction is learned in advance based on patches extracted from a set of fully-sampled training MR images.

5. The MRI apparatus of claim 1, wherein a dictionary used in the dictionary learning reconstruction is learned individually for each frequency band.

6. The MRI apparatus of claim 1, wherein the at least one processor is further configured to perform sparse decomposition by minimizing a number of non-zero elements in a patch represented as a linear combination of dictionary elements.

7. The MRI apparatus of claim 1, wherein each of k-spaces corresponding to the decomposed multiple frequency bands is composed of frequencies acquired from an initially reconstructed k-space corresponding to a current frequency band, while other frequency bands are filled with zeroes and marked as measured.

* * * * *